United States Patent [19]

Ikekawa et al.

[11] Patent Number: 5,206,230
[45] Date of Patent: Apr. 27, 1993

[54] FLUORINE-CONTAINING VITAMIN D3 ANALOGUES AND PHARMACEUTICAL COMPOSITION CONTAINING THE SAME

[75] Inventors: Nobuo Ikekawa, Musashino; Yoshiro Kobayashi, Tokyo; Takeo Taguchi, Hachioji, all of Japan; Yoko Tanaka, Delmar, N.Y.; Yutaka Ohira, Tsukuba, Japan

[73] Assignee: Daikin Industries Ltd., Osaka, Japan

[21] Appl. No.: 710,396

[22] Filed: Jun. 5, 1991

[51] Int. Cl.[5] .................. A01N 45/00; A61K 31/59; C07F 7/04
[52] U.S. Cl. .................. 514/167; 556/436; 556/449; 552/547
[58] Field of Search .............. 556/436, 449; 514/167; 552/547

[56] References Cited

U.S. PATENT DOCUMENTS

| | | | |
|---|---|---|---|
| 4,613,594 | 9/1986 | Baggiolini et al. | 556/436 |
| 4,717,721 | 1/1988 | De Luca et al. | 514/167 |

OTHER PUBLICATIONS

Hirobumi Tamaka et al., Seikagaku (Biochemistry), vol. 55 1323 (1983).
Colton et al., Lancet, Jan. 28, 188 (1989).
Ostrem et al. Proc. Natl. Acad. Sci. 84, 2610, (1987).
Baggiolini et al. JACS 104, 2945 (1982).
Toh et al., J. Org. Chem vol. 48, 1414, 1983.
Wovkulich et al. Tetrahedron vol. 40, 2283, (1984).
Augeron et al., Cancer Res. vol. 44, 3961, 1984.
Kay W. Colston et al, *The Lancet*, Jan. 28, 1989, pp. 188-191.
Voula K. Ostem et al, *Proc. Natl. Acad. Sci.*, USA, vol. 84 May 1987, pp. 2610-2614.

*Primary Examiner*—José G. Dees
*Assistant Examiner*—Joseph M. Conrad, III
*Attorney, Agent, or Firm*—Birch, Stewart, Kolasch & Birch

[57] ABSTRACT

Fluorine-containing vitamin D3 analogues of the formula[I]:

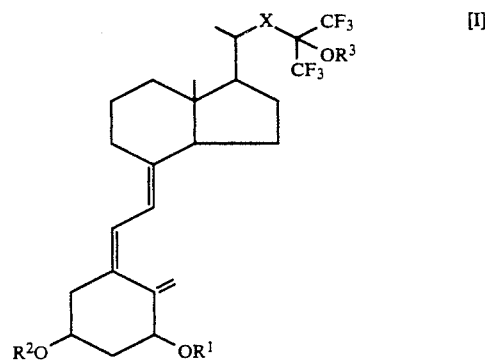

wherein $R^1$, $R^2$ and $R^3$ are independently hydrogen atom, a chemically inactive hydroxy-protecting group, an acyl having 2 to 8 carbon atoms, or an alkyl having 1 to 8 carbon atoms, X is a straight carbon chain having 4 to 6 carbon atoms which contains at least one double or triple bond, which have excellent vitamin D3-like activities, particularly anti-tumor activity owing to differentiation-inducing activity and are useful for the prophylaxis and treatment of various tumors, and intermediates therefor.

5 Claims, No Drawings

FLUORINE-CONTAINING VITAMIN D3 ANALOGUES AND PHARMACEUTICAL COMPOSITION CONTAINING THE SAME

This invention relates to novel fluorine-containing vitamin D3 analogues having excellent pharmacological activities and a pharmaceutical composition having vitamin D3-like activities and anti-tumor activity due to differentiation-inducing activity which contains the fluorine-containing vitamin D3 analogue as an active ingredient.

PRIOR ART

It is known that a bio-metabolite of vitamin D3, 1α,25-dihydroxyvitamin D3 is called an "active-type vitamin D3" and has an activity of promoting absorption of calcium via intestinal tract and thereby is useful as a medicament for the treatment of bone diseases. Recently, it has been found that the active-type vitamin D3 and analogues thereof have a differentiation-inducing activity for recovering normal cells from cancerated cells (cf. Hirobumi Tanaka et al., "Seikagaku" (Biochemistry), Vol. 55, 1323, 1983) and further that some of these compounds have a remarked activity of inhibiting the progress of cancer (K.W. Colton et al., Lancet, Jan. 28, 188, 1989). It has, however, been known that these active-type vitamin D compounds have high antagonistic activity against calcium metabolism which induces hypercalcaemia and hence can not be used in a high dose. Accordingly, these compounds are not necessarily usable for the treatment of diseases which require continuous administration in a comparatively high dose, for example, for the treatment of leukemia.

It has also been reported that 24-homo-1α, 25-dihydroxyvitamin D3, which has one longer carbon chain than the natural 1α, 25-dihydroxyvitamin D3, may also be usable as an anti-tumor drug (cf. V.K. Ostrem et al., Proc. Natl. Acad. Sci , 84, 2610, 1987). However, these vitamin D3 analogues have still a problem of side effect of hypercalcaemia and hence are still not insufficiently used as anti-tumor drug or anti-rheumatic drug.

It is described in WO 83/00335 (PCT/US82/00909) that hexafluoro-vitamin D derivatives of the following formula have high vitamin D-like activities.

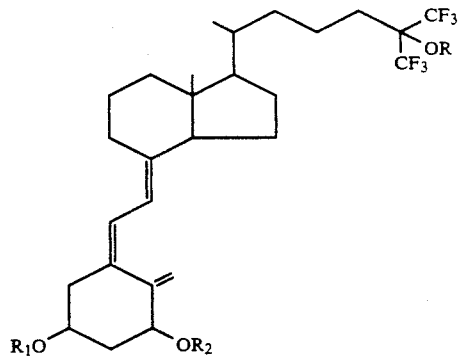

wherein R, R1 and R2 are independently hydrogen atom or an acyl having 1 to 4 carbon atoms.

SUMMARY DESCRIPTION OF THE INVENTION

The present inventors have intensively studied as to novel vitamin D3 analogues which have high action-selectivity with less side effect, that is, have potent pharmacological activities and lower toxicity, and have found that hexafluoro-24-homo-1α, 25-dihydroxyvitamin D3 has the desired properties.

An object of the invention is to provide novel fluorine-containing vitamin D3 analogues having high action-selectivity with less toxicity, more particularly, having pharmacological activities the same or superior to those of the known vitamin D3 compounds, especially anti-tumor activity owing to the cell differentiation-inducing activity. Another object of the invention is to provide a pharmaceutical composition having vitamin D3-like activities which contains as an active ingredient the fluorine-containing vitamin D3 analogue. A further object of the invention is to provide a novel intermediate suitable for the preparation of the active fluorine-containing vitamin D3 analogues. These and other objects and advantages of the invention will be apparent to the skilled persons in this field from the following description.

DETAILED DESCRIPTION OF THE INVENTION

The fluorine-containing vitamin D3 analogues of this invention are 24-homo-26,26,26,27,27,27-hexafluoro-1α, 25-dihyroxyvitamin D3 of the formula [I]:

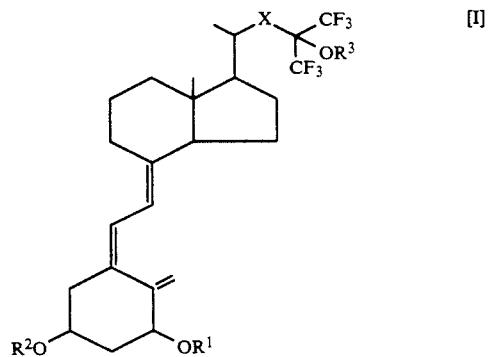

wherein $R^1$, $R^2$ and $R^3$ are independently hydrogen atom, a chemically inactive hydroxy-protecting group, an acyl having 2 to 8 carbon atoms, or an alkyl having 1 to 8 carbon atoms, X is a straight carbon chain having 4 to 6 carbon atoms which contains at least one double or triple bond.

In the present specification and claims, the chemically inactive hydroxy-protecting group denotes a group being capable of forming acetal-like group (e.g. methoxymethyl, methoxyethoxymethyl, tetrahydropyranyl, etc.), a silyl ether type protecting group (e.g. trimethylsilyl, t-butyldimethylsilyl, t-butyldiphenylsilyl, etc.), and the like, among which t-butyldimethylsilyl is particularly preferable, but is not limited thereto. The acyl having 2 to 8 carbon atoms includes an alkanoyl having 2 to 8 carbon atoms and having optionally a halogen substituent (e.g. acetyl, chloroacetyl, propionyl, pivaloyl, etc.), an aromatic acyl having 7 to 8 carbon atoms and having optionally a halogen or nitro substituent (e.g. benzoyl, p-chlorobenzoyl, p-nitrobenzoyl, etc.), among which acetyl and benzoyl are particularly preferable, but it is not limited thereto. The alkyl having 1 to 8 carbon atoms includes straight chain or branched chain alkyl groups having 1 to 8 carbon atoms (e.g. methyl, ethyl, propyl, isopropyl, n-butyl, t-butyl, n-pentyl, n-hexyl, n-octyl, etc.) and alkyl groups substituted by an aromatic group such as a phenyl having optionally a substituent selected from a halogen and an alkyl having 1 to 4 carbon atoms (e.g. benzyl, p-chlorobenzyl, p-methoxybenzyl, etc.).

Suitable examples of the compounds [I] are as follows.

26,26,26,27,27,27-Hexafluoro-24-homo-$\Delta^{22}$-1α, 25-dihydroxyvitamin $D_3$ (Compound A)

1α-t-Butyldimethylsilyloxy-26,26,26,27,27,27-hexafluoro-24-homo-25-hydroxy$\Delta^{22}$-vitamin $D_3$-3η-t-butyldimethylsilyl ether (Compound B)

26,26,26,27,27,27-Hexafluoro-24-homo-$\Delta^{24}$-1$\Delta$,25-dihydroxyvitamin $D_3$ (Compound C)

1α-t-Butyldimethylsilyloxy-26,26,26,27,27,27-hexafluoro-24-homo-25-hydroxy-$\Delta^{24}$-vitamin $D_3$-3β-t-butyldimethylsilyl ether (Compound D)

26,26,27,27,27-Hexafluoro-24-homo-$\Delta$-$^{22}$, $\Delta^{24}$-1α,25-dihydroxyvitamin $D_3$ (Compound E)

26,26,26,27,27,27-Hexafluoro-24-homo-$\Delta^{23}$-1α, 25-dihydroxyvitamin $D_3$ (Compound F)

1α, 25-diacetoxy-26,26,26,27,27,27-hexafluoro-24-homo-24-yne-vitamin $D_3$-3β-acetate (Compound G)

26,26,26,27,27,27-Hexafluoro-24-homo-1α, 25-dihydroxy-24-yne-vitamin $D_3$ (Compound H)

1α-Tetrahydropyranyloxy-26,26,26,27,27,27-hexafluoro-24-homo$\Delta^{22}$-25-hydroxy-24-yne-vitamin $D_3$-3β-tetrahydropyranyl ether (Compound I)

26,26,26,27,27,27-Hexafluoro-24-homo-1α-hydroxy-25-methoxymethoxy-23-yne-vitamin $D_3$ (Compound J)

26,26,26,27,27,27-Hexafluoro-24-homo-$\Delta^{22}$-25-methoxy-1α-pivaloyloxy-24-yne-vitamin $D_3$β-pivaloate (Compound K)

1α-Benzoyloxy-26,26,26,27,27,27-hexafluoro-24-homo-$\Delta^{22}$-25-methoxy-24-yne-vitamin $D_3$-3β-benzoate (Compound L)

1α-p-Methoxybenzyloxy-26,26,26,27,27,27-hexafluoro-24-homo-$\Delta^{22}$-25-hydroxyvitamin $D_3$-3β-p-methoxybenzyl ether (Compound M)

1α-t-Butyldimethylsilyloxy-25-trimethylsilyloxy-26,26,26,27,27,27-hexafluoro-24-homo-$\Delta^{24}$-vitamin $D_3$-3β-t-butyldimethylsilyl ether (Compound N)

The compounds [I] of this invention can be prepared by various processes. One of the best processes is illustrated below. A [ring C,D]fragment of the formula [II]:

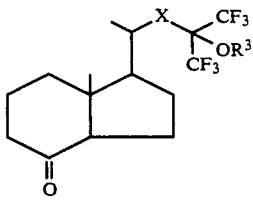

wherein $R^3$ is hydrogen atom, a chemically inactive hydroxy-protecting group, an acyl having 2 to 8 carbon atoms, or an alkyl having 1 to 8 carbon atoms, X is a straight carbon chain having 4 to 6 carbon atoms which contains at least one double or triple bond, is subjected to coupling reaction with an anion derived from a protected [ring A]fragment of the formula [III]:

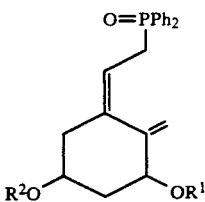

wherein $R^1$ and $R^2$ are independently hydrogen atom, a chemically inactive hydroxy-protecting group, an acyl having 2 to 8 carbon atoms, or an alkyl having 1 to 8 carbon atoms, and Ph means phenyl, to give a condensed product of the formula [I], optionally followed by removing the hydroxy-protecting group in the compound [I]to give a compound of the formula [IV]:

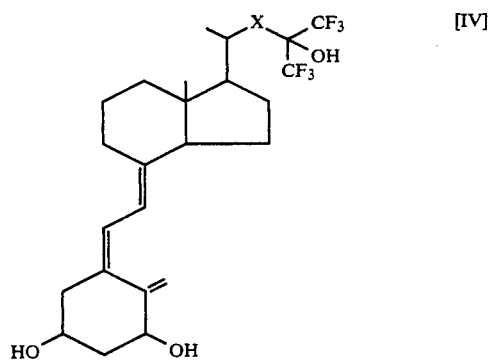

wherein X is as defined above.

The above coupling reaction of the compound [II] and the compound [III] is usually carried out at a low temperature, for example lower than −20° C., preferably −80° to −40° C., under an inert atmosphere (e.g. under argon gas) in an inert solvent (e.g. a cyclic ether, preferably tetrahydrofuran (THF), etc.). In this reaction, it is preferable to firstly convert the phosphine oxide compound [III] into the corresponding carbanion by treating the phosphine oxide compound in an inert solvent such as a lower alkane (e.g. hexane, etc.) at a low temperature as mentioned above with an alkyllithium (e.g. n-butyllithium, etc.) and then to subjected to the coupling reaction-with the compound [II]. The obtained product [I] can be purified by a conventional method, for example, by silica gel chromatography.

The removal of the hydroxy-protecting group from the compound [I] can be carried out by a conventional method. For example, in case of t-butyldimethylsilyl protecting group, the protected compound [I] is treated with a silyl ether cleaving agent (e.g. tetra-n-butylammonium fluoride, etc.) in an inert solvent (e.g. a cyclic ether, preferably tetrahydrofuran) at a temperature of from −20° C. to 50° C, usually at room temperature.

The starting compound [III] used in the above coupling reaction is prepared by a known process as disclosed in E.G. Baggiolini et al., J. Am. Chem. Soc., Vol. 104, 2945, 1982 and Japanese Patent First Publication (Kokai) No. 250844/1990.

On the other hand, another starting compound [II] is a novel compound. Thus, another object of this invention is to provide the novel intermediate.

The compound [II] may be prepared by various processes but is advantageously prepared by the following process. As one of the best embodiments, a process for preparing a compound of the formula [II] wherein R³ is hydrogen atom and contains a double bond at 2-position of the side chain (X), that is, [1R-[1α(R*),3αβ, 7αβ]]-octahydro-1-[7,7,7-trifluoro-6-hydroxy -1-methyl-6-trifluoro-methyl-2-heptenyl]-7a-methyl-1H-inden-4-one (Compound IIa) is illustrated by the following reaction scheme:

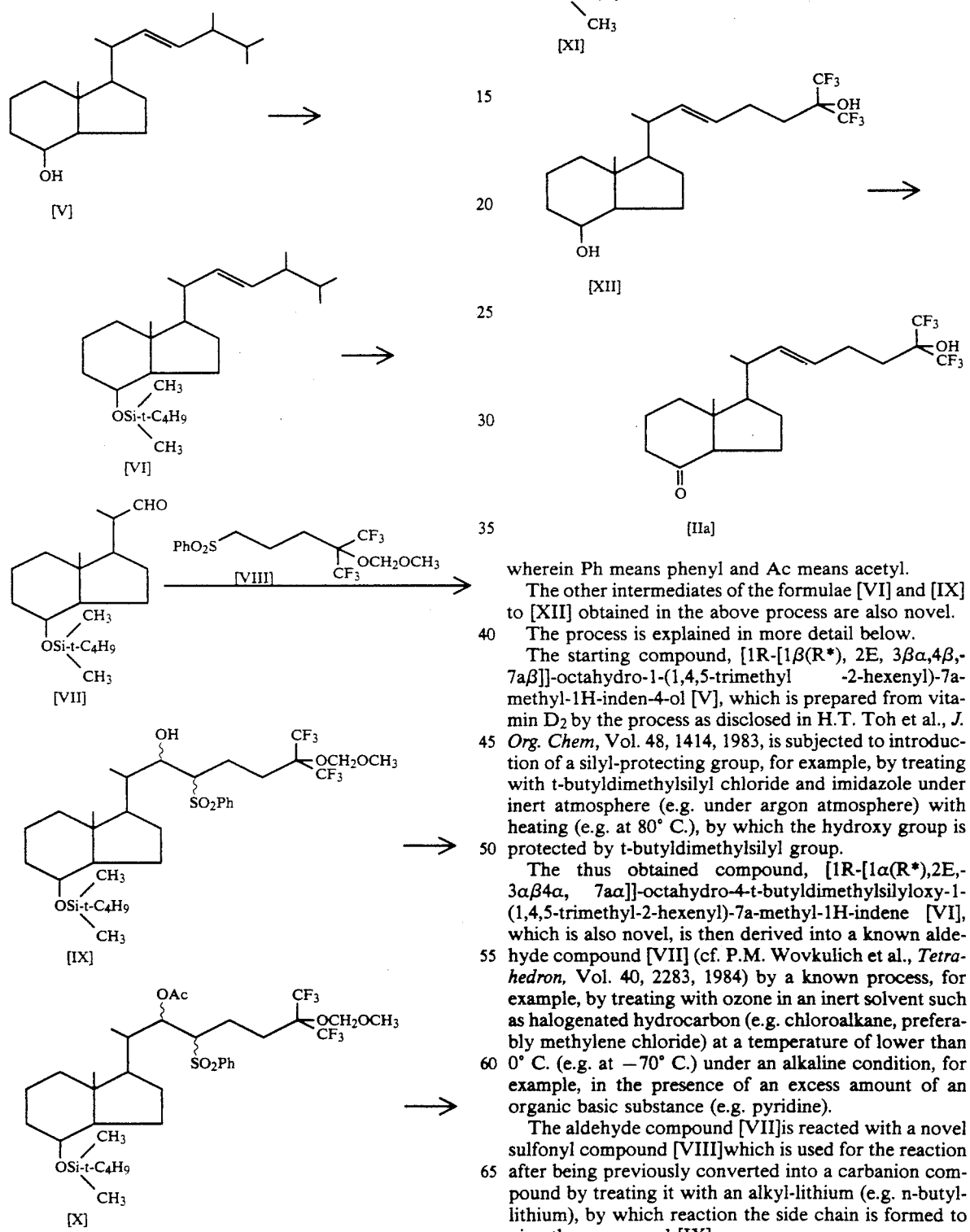

wherein Ph means phenyl and Ac means acetyl.

The other intermediates of the formulae [VI] and [IX] to [XII] obtained in the above process are also novel.

The process is explained in more detail below.

The starting compound, [1R-[1β(R*), 2E, 3βα,4β,-7aβ]]-octahydro-1-(1,4,5-trimethyl -2-hexenyl)-7a-methyl-1H-inden-4-ol [V], which is prepared from vitamin D₂ by the process as disclosed in H.T. Toh et al., J. Org. Chem, Vol. 48, 1414, 1983, is subjected to introduction of a silyl-protecting group, for example, by treating with t-butyldimethylsilyl chloride and imidazole under inert atmosphere (e.g. under argon atmosphere) with heating (e.g. at 80° C.), by which the hydroxy group is protected by t-butyldimethylsilyl group.

The thus obtained compound, [1R-[1α(R*),2E,-3αβ4α, 7αα]]-octahydro-4-t-butyldimethylsilyloxy-1-(1,4,5-trimethyl-2-hexenyl)-7a-methyl-1H-indene [VI], which is also novel, is then derived into a known aldehyde compound [VII] (cf. P.M. Wovkulich et al., Tetrahedron, Vol. 40, 2283, 1984) by a known process, for example, by treating with ozone in an inert solvent such as halogenated hydrocarbon (e.g. chloroalkane, preferably methylene chloride) at a temperature of lower than 0° C. (e.g. at −70° C.) under an alkaline condition, for example, in the presence of an excess amount of an organic basic substance (e.g. pyridine).

The aldehyde compound [VII] is reacted with a novel sulfonyl compound [VIII] which is used for the reaction after being previously converted into a carbanion compound by treating it with an alkyl-lithium (e.g. n-butyl-lithium), by which reaction the side chain is formed to give the compound [IX].

The compound [IX] is obtained in the form of a mixture of diastereomers at 2- and 3-positions of the side chain. The compound [IX] is then acylated with a conventional acylating agent, for example, acetylated with acetic anhydride to give the compound [X]. The acylated compound [X] is treated with an alkali metal or an alkali metal amalgam in the presence of an alkali metal phosphate in an inert solvent such as a lower alkanol, a cyclic ether or a mixture thereof, by which the arylsulfonyl group and acetoxy group are removed to form a double bond in the side chain. The preferred reactant is sodium amalgam and disodium hydrogen phosphate. The preferred solvent is methanol, tetrahydrofuran, or a mixture thereof. The above reaction is preferably carried out by adding the alkali metal amalgam to the mixture of the compound [X] in an inert solvent under cooling, preferably at about 0° C. to give the alkene compound [XI].

After purifying the thus obtained alkene compound [XI] by a conventional purification method, for example, by silica gel chromatography, the compound [XI] is treated with an organic or inorganic acid (e.g. acetic acid, hydrochloric acid, or a mixture thereof) in an inert solvent such as a halogenated hydrocarbon (e.g. chloroalkane, preferably methylene chloride), by which the protecting groups such as methoxymethyl group and t-butyldimethylsilyl group are removed to give the compound [XII].

The thus obtained compound [XII] is purified by a conventional purification method, for example, by silica gel chromatography, and then treated with an oxidizing agent such as a salt of cromic acid with an organic amine (e.g. pyridinium halochromate, preferably pyridinium chlorochromate) to give the desired compound [IIa]. The reaction is preferably carried out in an inert solvent such as a halogenated hydrocarbon (e.g. chloroalkane, preferably methylene chloride) under atmospheric conditions. The compound [IIa] can be purified by a conventional purification method, for example, by silica gel chromatography.

Another representative compound of the formula [II] wherein $R^3$ is hydrogen atom and contains a double bond at 4-position of the side chain (X), that is, [1R-[1α(R*), 4E, 3aβ, 4α,7aα]]-octahydro-1-[7,7,7-trifluoro-6-hydroxy-1-methyl-6-trifluoromethyl-4-heptenyl]-7a-methyl-1H-inden-4-one (Compound IIb) is prepared by a process as shown in the following reaction scheme:

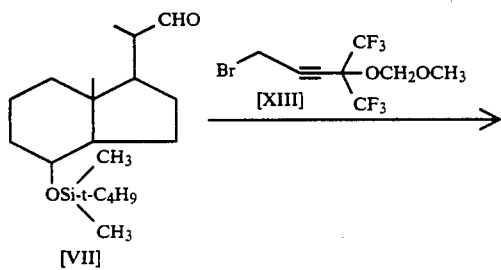

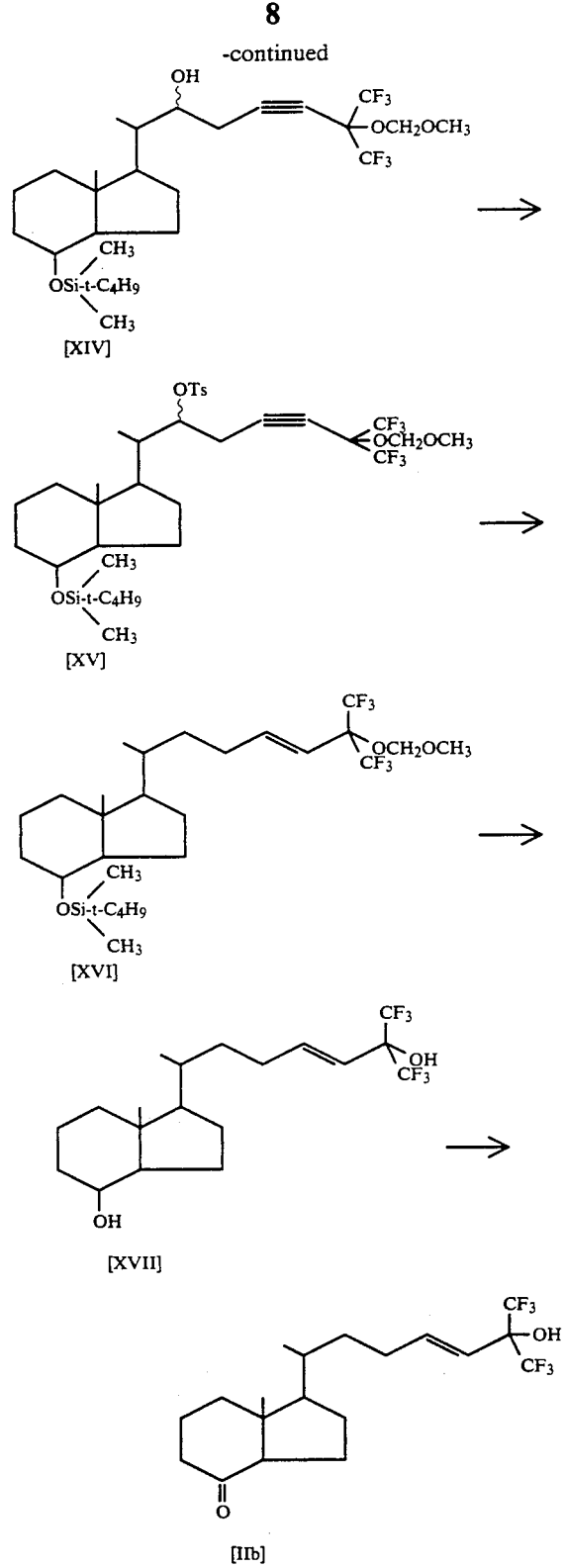

wherein Ts means p-tolyenesulfonyl.

The other intermediates of the formulae [XIV] to XVII] obtained in the above process are also novel.

The process is explained in more detail below.

The starting aldehyde compound [VII] is reacted with a novel acetylene compound [XIII] in an inert solvent such as an aprotic polar solvent (e.g. dimethylformamide, etc.) under inert atmosphere (e.g. argon atmosphere) in the presence of a metal (e.g. zinc) at a temperature of from $-10°$ C. to 50° C., preferably at room temperature, by which the side chain is formed to give the alcohol compound [XIV].

In the above step for preparing the compound [XIV], there are produced two optical isomers owing to the asymmetric carbon at 2-position in the side chain, but these isomers may optionally be separated in this step or in the next step for preparing the compound [XV] by a conventional separation method, for example, by silica gel chromatography or recrystallization.

The alcohol compound [XIV] obtained above is then tosylated by a conventional method, for example, by treating it with p-toluenesulfonyl chloride in pyridine to give the compound [XV].

After purifying the thus obtained compound [XV] by a conventional method, for example, by silica gel chromatography, the compound [XV] is treated with a reducing agent such as an alkali metal or alkali metal hydride (e.g. lithium aluminum hydride, etc.) in an inert solvent such as cyclic ether (e.g. tetrahydrofuran), at a temperature of 0° to 50° C., preferably 0° C. to room temperature, under inert atmosphere (e.g. argon atmosphere), by which there is produced the 4-trans-alkene compound [XVI].

After purifying by a conventional purification method, for example, by silica gel chromatography, the 4-trans-alkene compound [XVI] is treated with an organic or inorganic acid (e.g. acetic acid, hydrochloric acid, preferably a mixture thereof) in an inert solvent such as a halogenated hydrocarbon (e.g. chloroalkane, preferably methylene chloride), by which the protecting groups such as methoxymethyl group and t-butyldimethylsilyl group are removed to give the compound [XVII].

The thus obtained compound [XVII] is purified by a conventional purification method, for example, by silica gel chromatography, and then treated with an oxidizing agent such as a salt of cromic acid with an organic amine (e.g. pyridinium halochromate, preferably pyridinium chlorochromate) to give the desired compound [IIb]. The reaction is preferably carried out in an inert solvent such as a halogenated hydrocarbon (e.g. chloroalkane, preferably methylene chloride) under atmospheric conditions. The compound [IIb] can be purified by a conventional purification method, for example, by silica gel chromatography.

The novel fluorine-containing reagents [VIII] and [XIII] used in the above reactions can be prepared from 3-t-butyldimethylsilyloxy-1-propyne by a conventional process.

The fluorine-containing vitamin $D_3$ analogues [I] of this invention have excellent vitamin $D_3$-like activities, particularly anti-tumor activity, and are useful for the prophylaxis and treatment of abnormal cell growth, for example, tumors.

The compounds [I] of this invention can be administered by conventional methods, conventional types of unit dosages or with conventional pharmaceutical carrier or diluent to human beings and animals by oral route or parenteral route such as injections (e.g. intramuscular, subcutaneous, or intravenous injection). For the treatment of skin diseases, topical or external application is suitable.

For oral administration, the compounds [I] are usually formed in a conventional pharmaceutical preparation, in solid form such as tablets, capsules, granules, fine granules, powders, lozenge, troches, or in liquid form such as solutions, emulsions (e.g. water-in-oil type emulsions), suspensions or syrups. When formed into tablets or other solid preparations, one or more of the compounds [I] are admixtured with conventional excipients (e.g. sodium citrate, lactose, microcrystalline cellulose, starch, etc.), lubricating agents (e.g. anhydrous silicic acid, hydrized castor oil, magnesium stearate, sodium lauryl sulfate, talc, etc.), binding agents (e.g. starch paste, glucose, lactose, gum acacia, gelatin, mannitol, etc.), and any other conventional additives such as flavors, colorants, preservatives including antioxidants, surfactants, dispersing agents, emulsifiers, and the like and the mixture is formed into the desired preparation in a conventional manner. For liquid preparations, conventional liquid carriers such as water, physiological saline solution, oil, etc. are used.

For parenteral administration, the compound [I] is used in a sterilized oily or aqueous preparation. Injection preparation is usually prepared by dissolving the acitve compound [I] in water for injection, if necessary, followed by buffering or making isotonic with glucose, saline, or the like. External preparations include liquid and semi-liquid preparations such as liniments, lotions, applications, water-in-oil or oil-in-water type emulsions (e.g. creams), ointments, solutions, suspensions, drops, and the like. These preparations can be prepared by a conventional method and may also be incorporated with conventional additives such as excipients, binding agents, surfactants, flavors, colorants, emulsifiers, and the like.

The pharmaceutical preparations contains the active compound [I] of this invention in an amount of 1 ppm to 0.1% by weight and further may also contain other therapeutically active medicaments in addition to the active compound [I] of this invention.

The dosage of the compound [I] of this invention may somewhat vary in accordance with the administration methods, sex and age of the patient, severity of disease, and the like, but for oral administration the compound [I] is usually used in a dose of 0.1 to 500 $\mu$g per day, preferably 0.1 to 200 $\mu$g per day, in adult. For parenteral administration by injection, the dose may be decreased as usual.

The compounds of this invention and preparation thereof are illustrated by the following Examples and Experiments, but should not be construed to be limited thereto.

Example 1

Preparation of [1R-(1$\alpha$(R*),2E,3a$\beta$, 4$\alpha$,7a$\alpha$]]-octa-hydro-4-t-butyldimethylsilyloxy-1 -(1,4,5-trimethyl-2-hexenyl)-7a-methyl-1H-indene (Compound VI)

[1R-(1$\alpha$(R*),2E,3a$\beta$,4$\alpha$,7a$\alpha$]]-Octahydro-4-t-butyldimethylsilyloxy-1-(1,4,5 -trimethyl-2-hexenyl)-7a-methyl-1H-inden-4-ol (Compound V) (1.717 g, 6.17 mmol) is dissolved in N,N-dimethylformamide (abbreviated as DMF) (15 ml), and thereto are added imidazole (3.22 mg, 7.7 equivalents) and t-butyldimethylsilyl chlorine (3.93 g, 4.2 equivalents) in this order, and the mixture is stirred on water bath at about 80° C. under argon gas for 3 hours. After allowing to cool, the reaction mixture is poured into ice water and extracted with hexane. The organic layer is washed with saturated saline solution and dried over anhydrous magnesium sulfate. After distilling off the solvent, the residue is purified by silica gel column chromatography (eluant: hexane) to give the title compound (VI) (2.308 g, 95%).

$^1$H-NMR (CDCl$_3$) δ: 0.03 (s, 6H), 0.82 (d, J=7Hz, 3H), 0.84 (d, J=7Hz, 3H), 0.92 (d, J=7Hz, 3H), 0.93 (s, 9H), 0.95 (s, 3H), 0.99 (d, J=7Hz, 3H), 4.00 (brs, 1H), 5.18 (m, 2H).

EXAMPLE 2

Preparation of [1R-(1α(R*),3aβ, 4α,7aα]]-octahydro-4-t-butyldimethylsilyloxy-α,7a-dimethyl-1H-inden-1-acetaldehyde (Compound VII)

The compound VI obtained in Example 1 (391 mg, 0.996 mmol) is dissolved in methylene chloride and thereto is added pyridine (0.21 ml, 2.6 equivalents), and the mixture is cooled to −78° C. and thereto is introduced ozone gas for 35 minutes at the same temperature. The ozone gas is replaced by oxygen gas, and the oxygen gas is introduced for 10 minutes, and thereafter, active zinc (0.31 g, 15.3 equivalents) and acetic acid (1.5 ml, 26 equivalents) are added to the mixture at the same temperature. The mixture is stirred at −78° C. for 20 minutes and further at 0° C. for 20 minutes. The reaction mixture is diluted with diethyl ether and filtered with celite. The filtrate is washed with diluted hydrochloric acid, saturated sodium hydrogen carbonate solution, and saturated saline solution in this order, and dried over anhydrous magnesium sulfate. After distilling off the solvent, the residue is purified by passing a short column of silica gel (eluant, hexane-ethyl acetate=10 : 1) to give the title compound (VII) (269 mg, 83 %).

$^1$H-NMR (CDCl$_3$)δ: 0.02 (s, 6H), 0.90 (s, 9H), 0.95 (s, 3H), 1.10 (d, J=7Hz, 3H), 4.05 (brs, 1H), 9.60 (d, J=3Hz, 1H).

EXAMPLE 3

Preparation of [1R-[1α(R*),3aβ,4α,7aα]]-octahydro-4-t-butyldimethylsilyloxy-1-[7,7,7-trifluoro-2-hydroxy-1-methyl-6-methoxymethoxy-4-phenylsulfonyl-6-trifluoromethyl-2-heptyl]-7a-methyl-1H-indene (Compound IX)

1-Phenylsulfonyl-4-methoxymethoxy-4-trifluoromethyl-5,5,5-trifluoropentane (VIII) (200 mg, 0.558 mmol) is dissolved in THF, and thereto is added n-butyl-lithium (0.36 ml, 1.65 M) under argon gas at −78° C., and the mixture is stirred at −78° C. for 10 minutes. To the mixture is added a solution of the compound (VII) obtained in Example 2 (146 mg, 0.450 mmol) in THF (2 ml) at the same temperature. The mixture is stirred at −78° C. for 30 minutes, and thereto is added saturated aqueous ammonium chloride solution, and the reaction mixture is extracted with diethyl ether. The organic layer is washed with saturated saline solution and dried over anhydrous magnesium sulfate. After distilling off the solvent, the residue is purified by silica gel column chromatography (eluant, hexane-ethyl acetate=5 : 1) to give the title compound (IX) (288 mg, 89%).

$^1$H-NMR (CDCl$_3$) δ: 0.01 (s, 6H), 0.88 (s, 9H), 0.90 (s, 3H), 1.10 (d, J=7Hz, 3H), 3.07 (m, 1H), 3.42 (s, 3H), 4.00 (brs, 1H), 4.15 (m, 1H), 4.90 (brs, 2H), 7.58–7.90 (m, 5H).

IR (CHCl$_3$) 3500, 1150 cm$^{-1}$.

EXAMPLE 4

Preparation of [1R-[1α(R*),3aβ,4α,7aα]]-octahydro-4-t-butyldimethylsilyloxy-1-[2-acetoxy-7,7,7-trifluoro-1-methyl-6-methyoxymethoxy-4-phenylsulfonyl-6-trifluoromethyl-2-heptyl]-7a-methyl-1H-indene (Compound X)

The compound (IX) obtained in Example 3 (130 mg, 0.181 mmol) is dissolved in methylene chloride (2 ml), and thereto are added pyridine (0.87 ml, 48.5 equivalents), acetic anhydride (0.48 ml, 28 equivalents) and 4-dimethyl-aminopyridine (26 mg, 1.2 equivalent) under ice cooling, and the mixture is stirred at room temperature for 1.75 hour, and to the mixture is further added pyridine (4.7 ml, 262 equivalents), and the mixture is again stirred at room temperature overnight. To the mixture is added diluted hydrochloric acid, and the reaction mixture is extracted with diethyl ether. The organic layer is washed with saturated sodium hydrogen carbonate solution and saturated saline solution in this order, and dried over anhydrous magnesium sulfate. After distilling off the solvent, the residue is purified by silica gel column chromatography (eluant, hexane-ethyl acetate =5 : 1) to give the title compound (X) (128 mg, 93%).

$^1$H-NMR (CDCl$_3$)δ: 0.01 (s, 6H), 0.88 (s, 9H), 1.87 and 1.96 (s and s, 1H), 3.45 (s, 3H), 3.97 (brs, 1H), 4.92 (s, 2H), 4.50 (m, 1H), 7.56–7.93 (m, 5H).

EXAMPLE 5

Preparation of [1R-[1α(R*),2E,3aβ,4α,7aα]]-octahydro-4-t-butyldimethylsilyloxy-1-[7,7,7-trifluoro-6-methoxymethoxy-1-methyl-6-trifluoromethyl-2-heptenyl]-7a-methyl-1H-indene (Compound XI)

The compound (X) obtained in Example 4 (130 mg, 0.171 mmol) is dissolved in a mixture of THF (3 ml) and methanol (1 ml), and thereto is added anhydrous disodium hydrogen phosphate (512 mg, 21 equivalents), and the mixture is ice-cooled, and thereto is added 3 % sodium amalgam (0.60 g, 4.6 equivalents). The mixture is stirred at the same temperature for 15 minutes and further at room temperature for 30 minutes. The reaction mixture is diluted with diethyl ether, and the undissolved materials are filtered off, and the filtrate is washed with saturated saline solution and dried over anhydrous magnesium sulfate. After distilling off the solvent, the residue is purified by silica gel column chromatography (eluant, hexane) to give the title compound (XI) (78 mg, 81%).

$^1$H-NMR (CDCl$_3$)δ: 0.01 (s, 3H), 0.89 (s, 9H), 0.92 (s, 3H), 0.96 (d, J=7Hz, 3H), 3.47 (s, 3H), 4.00 (brs, 1H), 4.92 (s, 2H), 5.25 (dt, J=15Hz and 5Hz, 1H), 5.31 (dd, J=15Hz and 5Hz, 1H).

EXAMPLE 6

Preparation of [1R-[1α(R*),2E,3aβ,4α,7aα]]-octahydro-1-[7,7,7-trifluoro-6-hydroxy-1-methyl-6-trifluoromethyl-2-heptenyl]-7a-methyl-1H-inden-4-ol (Compound XII)

The compound (XII) obtained in Example 5 (80 mg, 0.143 mmol) is dissolved in methylene chloride (4 ml), and thereto are added acetic acid (2 ml) and diluted hydrochloric acid (2 ml), and the mixture is refluxed with stirring for 5 hours. After distilling off the solvent, the residue is diluted with chloroform, and the mixture is washed with 5% sodium hydrogen carbonate solution and saturated saline solution in this order, and dried over anhydrous magnesium sulfate. After distilling off the solvent, the residue is purified by flush silica gel column chromatography (eluant, hexane-ethyl acetate=3 : 1) to give the title compound (XII) (46.5 mg, 81%).

EXAMPLE 7

Preparation of
[1R-(1α(R*),2E,3aβ4α,7aβ]]-octa-hydro-1-[7,7,7-tri-fluoro
-6-hydroxy-1-methyl-6-trifluoromethyl-2-heptenyl]-7a-methyl-1H-inden-4-one (Compound IIa).

The compound (XII) (46.5 mg, 0.116 mmol) is dissolved in dichloromethane (2 ml), and thereto is added pyridinium chlorochromate (PCC) (60 mg, 2.4 equivalents), and the mixture is stirred under argon gas at room temperature for 1.5 hour. To the mixture is added diethyl ether, and the mixture is filtered with celite. The filtrate is distilled to remove the solvent, and the residue is purified by flush silica gel column chromatography (eluant, hexane-ethyl acetate = 3 : 1) to give the title compound (IIa) (35.7 mg, 77%).

$^1$H-NMR (CDCl$_3$)δ: 0.65 (s, 3H), 1.05 (d, J=7Hz, 3H), 3.26 (brs, 1H), 5.35 (dt, J=15Hz and 5Hz, 1H), 5.45 (dd, J=15Hz and 5Hz, 1H).

EXAMPLE 8

Preparation of
3-(t-butyldimethylsilyl)-1α-(t-butyldimethylsilyloxy)-26,26,26,27,27,27-hexafluoro-24-homo
25-hydroxy-Δ$^{22}$-Vitamin D$_3$ (Compound B)

A compound of the formula (III) wherein R$^1$ and R$^2$ are each t-butyldimethylsilyl (120 mg, 0.206 mmol, 2.4 equivalents) is dissolved in THF (4 ml), and the mixture is cooled to −78° C., and thereto is added n-butyl-lithium (0.16 ml, 1.6 M), and the mixture is stirred at the same temperature for 5 minutes. To the mixture is added a solution of the compound (IIa) obtained in Example 7 (34.7 mg, 0.087 mmol) in THF (2 ml) at −78° C. The mixture is stirred at the same temperature for 30 minutes, and thereto is added saturated sodium hydrogen carbonate solution. The mixture is extracted with ethyl acetate and the organic layer is washed with saturated saline solution and dried over anhydrous magnesium sulfate. After distilling off the solvent, the residue is purified by flush silica gel column chromatography (eluant, hexane-ethyl acetate =20 : 1) to give the title compound (B) (36.3 mg, 55%).

By the flush chromatography using an eluant having higher polarity (hexane-ethyl acetate = 1 : 1), the starting compound (III) (62.4 mg) is recovered.

$^1$H-NMR (CDCl$_3$)δ: 0.06 (s, 12H, Si-Me), 0.56 (s, 3H, 18-H), 0.87 (s, 18H, t-Bu), 1.02 (d, J=7Hz, 3H, 21-H), 2.44 (dd, J=10Hz and 3Hz, 1H, 4α-H), 2.82 (dd, J=12Hz and 3Hz, 1H, 9β-H), 4.19 (m, 1H, 3-H), 4.37 (m, 1H, 1H, 1-H), 4.86 (brs, 1H, 19E-H), 5.17 (brs, 1H, 19Z-H), 5.36 (dt, J=15Hz and 5Hz, 1H), 5.43 (dd, J=15Hz and 5Hz, 1H), 6.01 (d, J=11Hz, 1H, 7-H), 6.23 (d, J=11Hz, 1H, 6H).

EXAMPLE 9

Preparation of
26,26,26,27,27,27-hexafluoro-24-homo-Δ$^{22}$-1,25-dihydroxyvitamin D$_3$ (Compound A)

The compound (B) obtained in Example 8 (36.3 mg, 0.047 mmol) is dissolved in THF (1.6 ml), and thereto is added a solution of tetrabutylammonium fluoride in THF (0.32 ml, 1.0 M), and the mixture is stirred under argon gas at room temperature for 24 hours. After the solvent is distilled off, water is added to the residue, and the mixture is extracted with ethyl acetate. The organic layer is washed with water and saturated saline solution in this order, and dried over anhydrous magnesium sulfate. After distilling off the solvent, the residue is purified by flush silica gel column chromatography (eluant, hexane-ethyl acetate=1 : 2) and further purified by moderate pressure liquid chromatography (eluant, hexane-ethyl acetate =1 : 2) to give the title compound (A) (19.5 mg, 77%).

$^1$H-NMR (CDCl3) δ: 0.56 (s, 3H, 18-H), 1.03 (d, J=7Hz, 3H, 21-H), 2.60 (dd, J=10Hz and 3Hz, 1H, 4°-H), 2.83 (dd, J=12Hz and 3Hz, 1H, 9β-H), 4.22 (m, 1H, 3-H), 4.44 (m, 1H, 1H, 1-H), 5.00 (brs, 1H, 19E-H), 5.32 (brs, 1H, 19Z-H), 5.35 (dt, J=15Hz and 5Hz, 1H), 5.45 (dd, J=15Hz and 5Hz, 1H), 6.02 (d, J=11Hz, 1H, 7-H), 6.38 (d, J=11Hz, 1H, 6H).

EXAMPLE 10

Preparation of [1R-[1α(R*),3aβ,4α,7aα]]-octahydro-4-t-butyldimethylsilyloxy-1-[7,7,7-trifluoro-2-hydroxy-6-methoxymethoxy-1-methyl-6-trifluoromethyl-4-heptynyl]-7a-methyl-1H-indene (Compound XIV)

The compound (VII) obtained in Example 2 (165 mg, 0.508 mmol) and 5-bromo-2-methoxymethoxy-2-trifluoromethyl-5,5,5-trifluoropent-3-yne (XIII) (338 mg, 2.0 equivalents) are dissolved in DMF (1.2 ml), and thereto is added zinc dust (84 mg, 2.5 equivalents) under argon gas, and the mixture is stirred for 30 minutes. To the mixture is added saturated aqueous ammonium chloride solution, and the reaction mixture is extracted with diethyl ether. The organic layer is dried over anhydrous magnesium sulfate. After distilling off the solvent, the residue is purified by flush silica gel column chromatography (eluant, hexane-ethyl acetate=5 : 1) to give the compound (XIV-a) having R configuration at 2-position in the side chain (55 mg, 19%) and the compound (XIV-b) having S configuration at 2-position in the side chain (215 mg, 74%).

Compound (XIV-a):
$^1$H-NMR (CDCl$_3$) δ: 0.00 (s, 3H), 0.01 (s, 3H), 0.89 (s, 9H), 0.93 (d, J=5Hz, 3H), 0.95 (s, 3H), 3.48 (s, 3H), 3.89 (m, 1H), 4.00 (brs, 1H), 5.08 (d, J=25Hz, 1H), 5.10 (d, J=25Hz, 1H).

Compound (XIV-b):
$^1$H-NMR (CDCl$_3$)δ: 0.00 (s, 3H), 0.01 (s, 3), 0.90 (s, 9H), 0.91 (d, J=5Hz, 3H), 0.91 (s, 3H), 2.32 (dd, J=17Hz and 5Hz, 1H), 2.60 (dd, J=17Hz and 9Hz, 1H), 3.47 (s, 3H), 3.95 (m, 1H), 4.00 (brs, 1H), 5.07 (d, J=25Hz, 1H), 5.09 (d, J=25Hz, 1H).

EXAMPLE 11

Preparation of [1R-[1α(R*,S*),3aβ,4a,7aα]]-octahydro-4-t-butyldimethylsilyl-1-[7,7,7-trifluoro-6-methoxymethoxy-1-methyl-2-p-toluenesulfonyloxy-6-trifluoromethyl-4-heptynyl]-7a-methyl-1H-indene (Compound XV)

The compound (XIV-b) obtained in Example 10 (71 mg, 0.124 mmol) is dissolved in pyridine (1 ml), and thereto is added 4-dimethylaminopyridine (5 mg, 0.3 equivalent) and is further added p-toluenesulfonyl chloride (300 mg, 12.7 equivalents) with cooling under argon gas. The mixture is stirred at room temperature for 44.5 hours and thereafter diluted with diethyl ether. The mixture is washed with diluted hydrochloric acid, 2 % sodium hydrogen carbonate solution and saturated saline solution in this order. The organic layer is dried over anhydrous magnesium sulfate and distilled to remove the solvent. The residue is dissolved in THF (1 ml) and thereto is added 25 % aqueous ammonia (5 drops) under ice cooling, and the mixture is stirred at the same temperature for 10 minutes. After distilling off the solvent, the residue is purified by silica gel column chromatography (eluant, hexane-ethyl acetate=5:1) to give the title compound (XV) (75 mg, 83%).

$^1$H-NMR (CDCl$_3$)$\delta$: 0.00 (s, 3H), 0.01 (s, 3H), 0.84 (s, 3H), 0.87 (s, 9H), 0.91 (d, J=6Hz, 3H), 2.46 (s, 3H), 2.72-(dd, J=17Hz and 9Hz, 1H), 2.84 (dd, J=17Hz and 5Hz, 1H), 3.41 (s, 3H), 3.95 (m, 1H), 4.70 (m, 1H), 5.02 (s, 2H), 7.35 and 7.80 (each d, 4H, J=8Hz).

EXAMPLE 12

Preparation of [1R-[1α(R*),4E,3aβ,4α,7aβ]]-octahydro-4-t-butyldimethylsilyl-1-[7,7,7-trifluoro-6-methoxy-methoxy-1-methyl-6-trifluoromethyl-4-heptenyl]-7a-methyl-1H-indene (Compound XVI)

The compound (XV) obtained in Example 11 (42 mg, 0.0567 mmol) is dissolved in THF (0.5 ml), and thereto is added lithium aluminum hydride (40 mg, 18 equivalents) under ice cooling, and the mixture is stirred at room temperature for 10 minutes. To the mixture is added a small amount of ethyl acetate and the mixture is diluted with diethyl ether and thereto is further added methanol (2 ml). The organic layer is washed with diluted hydrochloric acid and saturated saline solution in this order, and dried over anhydrous magnesium sulfate. After distilling off the solvent, the residue is purified by silica gel column chromatography (eluant, hexane) to give the title compound (XVI) (26 mg, 81%

$^1$H-NMR (CDCl$_3$)$\delta$: 0.00 (s, 3H), 0.01 (s, 3H), 0.89 (s, 9H), 0.90 (s, 3H), 0.91 (d, J=7Hz, 3H), 3.45 (s, 3H), 4.00 (brs, 1H), 4.88 (s, 2H), 5.54 (d, J=16Hz, 1H), 6.26 (dt, J=15Hz and 7Hz, 1H).

EXAMPLE 13

Preparation of [1R-[1α(R*),4E,3aβ,4α,7aα]]-octahydro-1-[7,7,7-trifluoro-6-hydroxy-1-methyl-6-trifluoromethyl-4-heptenyl]-7a-methyl 1H-inden-4-ol (Compound XVII)

The compound (XVI) obtained in Example 12 (41 mg, 0.0731 mmol) is dissolved in methylene chloride (3 ml), and thereto are added acetic acid (3 ml) and diluted hydrochloric acid (0.6 ml), and the mixture is refluxed with stirring for 5 hours. After distilling off the solvent, the residue is diluted with chloroform and washed with 5% sodium hydrogen carbonate solution and saturated saline solution in this order and dried over anhydrous magnesium sulfate. After distilling off the solvent, the residue is purified by flush silica gel column chromatography (eluant, hexane-ethyl acetate =3:1) to give the title compound (XVII) (25 mg, 85%).

$^1$H-NMR (CDCl$_3$)$\delta$: 0.91 (d, J=6Hz, 3H), 0.92 (s, 3H), 4.08 (brs, 1H), 5.58 (d, J=16Hz, 1H), 6.29 (dt, J=16Hz and 7Hz, 1H).

EXAMPLE 14

Preparation of [1R-[1α(R*),4E,3aβ,4α,7aα]]-octahydro-1-[7,7,7-trifluoro-6-hydroxy-1-methyl-6-trifluoromethyl-4-heptenyl]-7a-methyl-1H-inden-4-one (Compound IIb)

The compound (XVII) obtained in Example 13 (29.0 mg, 0.072 mmol) is dissolved in dichloromethane (2 ml), and thereto is added pyridinium chlorochromate (44 mg, 2.8 equivalents), and the mixture is stirred at room temperature under argon gas for 2.5 hours. To the mixture is added diethyl ether, and the mixture is filtered with celite. The eluate is distilled to remove the solvent, and the residue is purified by flush silica gel column chromatography (eluant, hexane-ethyl acetate=3:1) to give the title compound (IIb) (27.0 mg, 94%).

$^1$H-NMR (CDCl$_3$)$\delta$: 0.63 (s, 3H), 0.97 (d, J=6Hz, 3H), 5.58 (d, J=16Hz, 1H), 6.29 (dt, J=16Hz and 7Hz, 1H).

EXAMPLE 15

Preparation of 3-(t-butyldimethylsilyl)-1α-(t-butyldimethylsilyloxy)-26,26,26,27,27,27-hexafluoro 24-homo-25-hydroxy-$\Delta^{24}$-vitamin D$_3$ (Compound D)

A compound of the formula (III) wherein R$^1$ and R$^2$ are each t-butyldimethylsilyl (150 mg, 0.257 mmol, 2.1 equivalents) is dissolved in THF (4 ml), and the mixture is cooled to −78° C., and thereto is added n-butyl-lithium (0.20 ml, 1.6 M), and the mixture is stirred at the same temperature for 5 minutes. To the mixture is added a solution of the compound (IIb) obtained in Example 14 (50 mg, 0.125 mmol) in THF (2 ml) at −78° C. The mixture is stirred at the same temperature for 30 minutes, and thereto is added saturated sodium hydrogen carbonate solution. The mixture is extracted with ethyl acetate and the organic layer is washed with saturated saline solution and dried over anhydrous magnesium sulfate. After distilling off the solvent, the residue is purified by flush silica gel column chromatography (eluant, hexane-ethyl acetate=20:1) to give the title compound (D) (45 mg, 47%).

By the flush chromatography using an eluant having higher polarity (hexane-ethyl acetate =1:1), the starting compound (III) (120 mg) is recovered.

$^1$H-NMR (CDC13) $\delta$: 0.06 (s, 12H, Si-Me), 0.53 (s, 3H, 18-H), 0.88 (s, 18H, t-Bu), 0.94 (d, J=7Hz, 3H, 21-H), 2.44 (dd, J=12Hz and 3Hz, 1H, 4° -H), 2.82 (dd, J=11Hz and 3Hz, 1H, 9β-H), 4.18 (m, 1H, 3-H), 4.38 (m, 1H, 1-H), 4.86 (brs, 1H, 19E-H), 5.18 (brs, 1H, 19Z-H), 5.58 (d, J=16Hz, 1H, 24-homo-H), 6.02 (d, J=11Hz, 1H, 7-H), 6.24 (d, J=11Hz, 1H, 6-H), 6.26 (dt, J=16Hz and 7Hz, 1H, 24-H).

EXAMPLE 16

Preparation of 26,26,26,27,27,27-hexafluoro-24-homo-$\Delta^{24}$-1α, 25-dihydroxyvitamin D$_3$ (Compound C)

The compound (D) obtained in Example 15 (45 mg, 0.059 mmol) is dissolved in THF (2 ml), and thereto is added a solution of tetrabutylammonium fluoride in THF (0.30 ml, 1.0 M), and the mixture is stirred under argon gas at room temperature for 24 hours. After the solvent is distilled off, water is added to the residue, and the mixture is extracted with ethyl acetate. The organic layer is washed with water and saturated saline solution in this order, and dried over anhydrous magnesium sulfate. After distilling off the solvent, the residue is purified by flush silica gel column chromatography (eluant, hexane-ethyl acetate =1:2) and further purified by moderate pressure liquid chromatography (eluant, hexane-ethyl acetate=1:2) to give the title compound (C) (11.7 mg, 37%).

$^1$H-NMR (CDC13) $\delta$: 0.54 (s, 3H, 18-H), 0.95 (d, J=6Hz, 3H, 21-H), 2.60 (dd, J=11Hz and 3Hz, 1H, 4α-H), 2.83 (dd, J=12Hz and 3Hz, 1H, 9β-H), 4.23 (m, 1H, 3-H), 4.43 (m, 1H, 1-H), 5.00 (brs, 1H, 19E-H), 5.33 (brs, 1H, 19Z-H), 5.58 (d, J=16Hz, 1H, 24-homo-H), 6.02 (d, J=11Hz, 1H, 7-H), 6.29 (dt, J=16Hz and 7Hz, 1H, 24-H), 6.38 (d, J=11Hz, 1H, 6-H).

EXPERIMENT

Test Method

Subculture cells (HT-29) derived from human colonic cancer were inoculated onto a 24-well plate for tissue culture and thereto was added calf serum in an amount of 10% by weight, which was cultured in RPMI-1640 medium. After culturing for 24 hours, the supernatant was removed. To the residue was added a medium containing $2 \times 10^{-3}$M sodium butyrate and 1α,25-dihydroxyvitamin $D_3$ or a vitamin $D_3$ analogue of this invention (exchange of the medium), and the mixture was subjected to station culture in a culture vessel containing carbon dioxide (5 % $CO_2$—95 % air) at 37° C. On every other day, the culture medium was exchanged with the same medium as mentioned above, and on 7th day, the number of the myxopoietic cells and shape of the cells were observed by the method of Augeron et al. [cf. *Cancer Res*, Vol. 44, 3961, 1984].

It is known that the myxopoiesis is observed in normal cells of large intestine (the colon) but not in cancerated cells. Accordingly, as a marker for measuring the fact that the caner cells HT-29 was differentiated and could express characteristic of normal cells, the number of mycopoietic cells was measured.

Results

The data obtained above were shown in percentage based on whole cells (200 cells) measured. The results are shown in the following Table 1.

TABLE 1

| Test compound | Concentration (M) | Number of myxopoietic cells (%) |
|---|---|---|
| Non | 0 | 3 ± 3 |
| 1α,25-dihydroxy-vitamin $D_3$ | $10^{-7}$ | 100 |
| 1α,25-dihydroxy-vitamin $D_3$ | $10^{-8}$ | 39 ± 0 |
| Compound A | $10^{-7}$ | 100 |
| Compound A | $10^{-8}$ | 99 ± 1 |
| Compound A | $10^{-9}$ | 44 ± 6 |
| Compound B | $10^{-7}$ | — |
| Compound B | $10^{-8}$ | — |
| Compound B | $10^{-9}$ | — |
| Compound C | $10^{-7}$ | 100 |
| Compound C | $10^{-8}$ | 94 ± 5 |
| Compound C | $10^{-9}$ | 42 ± 4 |

As is clear from the above results, when the HT-29 cells were treated by $2 \times 10^{-3}$M sodium butyrate and the compounds of this invention, the cells were differentiated into myxopoietic cells.

What is claimed is:

1. A fluorine-containing vitamin $D_3$ analogue of the formula [I]:

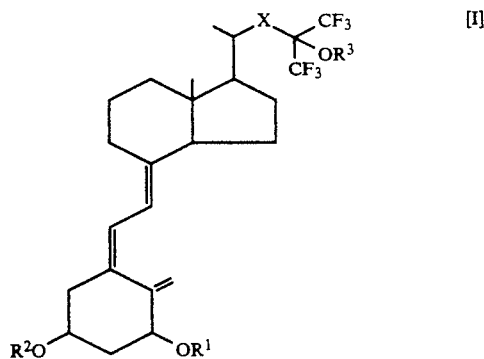

wherein $R^1$, $R^2$ and $R^3$ are independently hydrogen atom, a chemically inactive hydroxy-protecting group, an acyl having 2 to 8 carbon atoms, or an alkyl having 1 to 8 carbon atoms, X is a straight carbon chain having 4 to 6 carbon atoms which contains at least one double or triple bond at the 24-position.

2. The compound according to claim 1, wherein $R^1$, $R^2$ and $R^3$ are all hydrogen atom and X is a straight carbon chain having 4 carbon atoms which contain at least one double or triple bond at the 24 position.

3. The compound according to claim 1 which is a member selected from the following groups: dihydroxyvitamin $D_3$, and 1α-t-butyldimethylsilyloxy-26,26,26,27,27,27-hexafluoro-24-homo-25-hydroxy-$\Delta^{24}$-vitamin $D_3$-t-butyldimethylsilyl ether.

4. A pharmaceutical composition which comprises as an active ingredient an effective amount of the compound as set forth in claim 1 in admixture with a conventional pharmaceutically acceptable carrier or diluent.

5. A pharmaceutical composition which comprises as an active ingredient an effective amount of the compound as set forth in claim 2, in admixture with a conventional pharmaceutically acceptable carrier or diluent.

* * * * *